United States Patent [19]

Pierce, Jr.

[11] Patent Number: 5,242,937

[45] Date of Patent: Sep. 7, 1993

[54] TOPICALLY ACTIVE OCULAR THIADIAZOLE SULFONAMIDE CARBONIC ANHYDRASE INHIBITORS

[75] Inventor: William M. Pierce, Jr., Louisville, Ky.

[73] Assignee: Research Corporation Technologies, Inc., Tucson, Ariz.

[21] Appl. No.: 495,550

[22] Filed: Mar. 19, 1990

[51] Int. Cl.$^5$ ...................... A61K 31/38; A61K 31/41
[52] U.S. Cl. ................................. 514/363; 544/284; 546/113; 548/139; 548/141
[58] Field of Search ........................................ 514/363

[56] References Cited

U.S. PATENT DOCUMENTS

| | | | |
|---|---|---|---|
| 3,985,892 | 10/1976 | Roux et al. | 424/270 |
| 4,021,225 | 5/1977 | Hedrich et al. | 71/90 |
| 4,097,263 | 6/1978 | Kirkpatrick | 71/90 |
| 4,255,182 | 3/1981 | Krenzer | 71/90 |
| 4,305,927 | 12/1981 | Theeuwes et al. | 424/80 |
| 4,438,123 | 3/1984 | Smith et al. | 424/270 |
| 4,483,864 | 11/1984 | Barfknecht et al. | 424/270 |
| 4,483,872 | 11/1984 | Barfknecht et al. | 424/321 |
| 4,619,939 | 10/1986 | Maren | 514/363 |
| 4,629,738 | 12/1986 | Barfknecht et al. | 514/603 |
| 4,636,515 | 1/1987 | Barfknecht et al. | 514/363 |
| 4,975,446 | 12/1990 | Trager et al. | 514/363 |
| 5,010,204 | 4/1991 | Antonaroli et al. | 548/128 |

FOREIGN PATENT DOCUMENTS 0354881 2/1990 European Pat. Off. .

OTHER PUBLICATIONS

Katritzky, et al., J. Med. Chemistry, 1987 30:2058-2062.
Pierce, et al., Hormone Metab. Res., 1982, 14, 670.
Pierce, et al., Research Communications in Chemical Pathology & Pharmacology, 1985, 50:3-20.
Tinker, et al., The Journal of Pharmacology and Experimental Therapeutics, 1981, 218:600-607.
Maren, Journal of Pharmacology and Experimental Therapeutics, 1987, 241: 56-63.
Maren, Drug Development Research, 1987, 10:255-276.
Maren, et al., Exp. Eye Research, 1983, 36:457-480.
Duffel, et al., J. Med. Chemistry, 1986, 29, 1488-1494.
Kishida, et al., Exp. Eye Res., 1986, 43:981-995.
Antonaroli, et al., "Chemical Abstracts", vol. 113, 1990, col. 113; 152426h.

Primary Examiner—C. Warren Ivy
Assistant Examiner—James H. Turnipseed
Attorney, Agent, or Firm—Scully, Scott Murphy & Presser

[57] ABSTRACT

The present invention is directed to a compound of the formula:

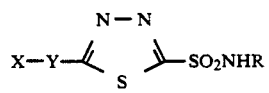

or pharmaceutically acceptable salts thereof which are useful in the treatment of glaucoma and in the assessment of corneal function.

4 Claims, No Drawings

TOPICALLY ACTIVE OCULAR THIADIAZOLE SULFONAMIDE CARBONIC ANHYDRASE INHIBITORS

BACKGROUND OF THE INVENTION

This invention relates to derivatives of thiadiazoles useful as carbonic anhydrase inhibitors (CAI) and pharmaceutically effective salts thereof. More particularly, the compounds of this invention are useful in the treatment of glaucoma and assessment of corneal function.

FIELD OF THE INVENTION

Carbonic anhydrase is an enzyme which secretes acidic or basic fluids in a variety of tissues, including the eye, pancreas, choroid plexus of the central nervous system, kidney, bone and stomach. Carbonic anhydrase mediated secretion is a target for pharmocotherapy and a host of pathologies. The compounds of the present invention are useful in the treatment of and prophylaxis of these pathologies, such as peptic ulcers disease (by inhibiting gastric ulcer secretion), altitude sickness, epilepsy, or as a diuretic.

Another pathological state characterized by inappropriate carbonic anhydrase secretion is metabolic bone disease, such as osteoporosis. The compound of the present invention inhibit bone resorption and are thus useful for the treatment and prophylaxis of metabolic bone disorders.

Glaucoma is another pathological state caused by inappropriate carbonic anhydrase mediated secretion. The compounds of the present invention are useful in the management of glaucoma and assessment of corneal function.

The term glaucoma refers to a group of eye diseases often characterized by elevated intraocular pressure (IOP). Accompanying this increased IOP is a restriction of blood supply to the optic nerve, and if uncontrolled, loss of vision. Much of the pharmacotherapeutic management of glaucoma is accomplished by use of agents which are autonomic nervous system agonists or antagonists The goal of such therapies is reduction in inflow of aqueous humor or improvement of outflow facility.

A class of drugs, the carbonic anhydrase inhibitors (CAI), have been used to diminish aqueous humor inflow by inhibition of carbonic anhydrase (CA) The prototypical CAI acetazolamide, was shown to decrease IOP following oral administration, B. Becker, *Am. J. Opthalmol.*, Vol. 38, pp. 16–17, 1954. Findings such as these with other CAI led to a flurry of hopeful research and clinical activity in the preparation of these drugs. The CAI are in general rather non-toxic, and oral administration of CAI does diminish IOP; however, the incidence and severity of side effects have limited patient compliance and hence clinical efficacy These side effects include depression, fatigue, anorexia and paresthesia. Due to the incidence of these side effects, upon systemic administration of inhibitors, topical administration has been attempted. Under these conditions, however, the most potent CAI (as determined in vitro) do not lower IOP. This is because transcorneal absorption of topically administered CAI yields inadequate drug concentrations in the target tissue, the ciliary epithelium.

Recently, efforts have been renewed in the quest for a topical CAI for the lowering of IOP. Several syntheses have yielded inhibitors which are effective in lowering IOP, T. H. Maren, et. al. Exp Eye Res., Vol. 36, pp. 457–480 (1983). One such agent, "aminozolamide," has been tested, and found to be partially effective in clinical trial, R. A. Lewis, et. al., *Arch Ophthalmol.*, Vol. 104, pp.842–844, 1986. Other routes have taken methazolamide and ethoxzolamide, classical inhibitors, and modified them to form compounds having a greater corneal permeability. Another approach has been used which involves the syntheses of prodrugs, M. F. Sugrue, et. al. *J. Pharmacol. Exp. Ther.*, Vol. 232, pp. 534–540 (1985), e.g., an ester of the hydroxy analogue of ethoxzolamide, which is subject to hydrolysis by esterases as it traverses the cornea, yielding an active inhibitor. Another new class of CAI has been produced which is effective as an ocular hypotensive agent as well, R. F. Wand, et. al., Abstracts of the Annual Meeting of the American Society for Research in Vision and Ophthalmology, p. 16 #7, 1988.

These studies have focused on topical delivery of novel CA inhibitors to diminish systemic side effects. The cornea is a barrier of mixed hydrophobic and hydrophilic properties, due to both cell and stromal layers. Successful penetration of the cornea requires then either (1) a drug which of itself has substantial aqueous and lipid solubilities or (2) a pro-drug which is lipophilic but is hydrolyzed by corneal epithelial esterases to yield a more hydrophilic, active drug.

The endothelium of the cornea is a cell layer on the posterior aspect of the cornea which functions to maintain a dehydrated, transparent cornea. Carbonic anhydrase plays a role in this dehydration function, and inhibition of corneal endothelial CA leads to transient corneal swelling. Administration of CAI topically to the cornea, followed by measurement of corneal thickness, yields a measure of corneal endothelial functional integrity. This allows the corneal surgeon to differentiate between sufficient and defective corneas, and supports the decision to transplant donor corneas.

SUMMARY OF THE INVENTION

This invention is directed to novel compounds useful in the treatment of glaucoma or assessment of corneal function having the general formula I:

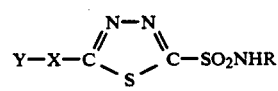

and pharmaceutically acceptable salts thereof, wherein

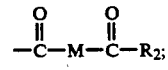

X is O, S, $NR_6$ or N; or
XY taken together is

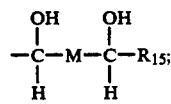

R is H or Lower alkyl;
$R_2$ is $OR_4$, $SR_4$, $NR_4R_5$, or represents a covalent bond connecting its adjacent carbonyl with X when X is N, thereby forming a cyclic structure of the formula:

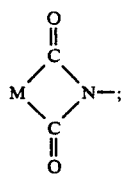

$R_{15}$ is hydrogen, lower alkyl, lower alkenyl, lower alkyny aryl, aryl lower alkyl or a nitrogen, sulfur or oxygen containing heterocyclic ring or represents a covalent bond connecting its adjacent carbinol group with X when X is N, thereby forming a cyclic structure of the formula:

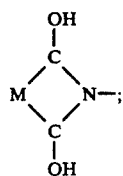

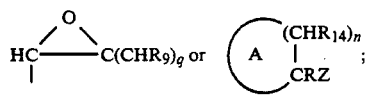

Z is hydrogen, or lower alkyl;

ring A is an alicyclic, aromatic ring or oxygen, nitrogen or sulfur containing heterocyclic ring, contains from 5 to 14 ring atoms and may be unsubstituted or substituted with at least one substituent selected from the group consisting of lower alkyl, aryl, aryl lower alkyl, carboxy, OH, carboloweralkoxy, formyl, lower alkanoyl, lower alkoxy, $SR_3$ or $NR_3R_7$;

$R_3$, $R_7$ and $R_6$ are independently hydrogen or lower alkyl;

$R_4$ and $R_5$ are independently H, lower alkyl, aryl or aryl lower alkyl;

each $R_9$ can be the same or different and is H, lower alkyl, aryl, aryl lower alkyl, $OR_{10}$, $SR_{10}$ or $NR_{10}R_{11}$;

each $R_{10}$ and $R_{11}$ can be the same or different and is H, lower alkyl, aryl, aryl lower alkyl, lower alkanoyl or aroyl;

$R_{14}$ is H or lower alkyl or $R_{14}$ and Z taken together form a covalent bond;

p is 0–6;

q is 0–4; and n is or 1.

In a preferred embodiment R is hydrogen thereby defining the —$SO_2NH_2$ moiety.

The lower alkyl groups, when used singly or in combination with other groups, contain from one to six carbon atoms and may be straight chain or branched. This group includes such groups as methyl, ethyl, propyl, isopropyl, butyl, sec-butyl, t-butyl, isobutyl, amyl, hexyl and the like. In a preferred form the lower alkyl groups have from one to four carbon atoms.

The lower alkenyl groups contain from two to six carbon atoms and may be straight chain or branched. This group includes both the "Z" and "E" isomers. Examples include ethenyl, 1-propenyl, 2-propenyl, 2-methyl-1-propenyl, and the like.

The lower alkynyl groups contain from two to six carbon atoms and may be straight chain or branched. This group includes such substituents as ethynyl, 1-propynyl, 2-propenyl, 2-methyl-1-propynyl and the like.

The aryl groups, when used singularly or in combination with other groups include aromatic radicals containing from six to ten ring carbon atoms and up to a total of 15 carbon atoms. These may be unsubstituted or substituted with $OR_4$, $NR_4R_5$ or $SR_4$. They include groups such as phenyl, α and β-napthyl. The preferred aryl is phenyl. In a preferred form aryl lower alkyl includes alkyl group bonded to an aryl group, whereby the substituent is connected to the main chain through the "alkylene" bridge. This group includes benzyl, phenethyl and the like.

The alicyclic rings contain from five to eight ring carbon atoms and up to 12 total carbon atoms. This may be fully saturated or partially saturated i.e., contain double or triple bonds. These may be unsubstituted or substituted with $OR_4$, $NR_5R_6$ or $SR_4$. In a preferred form the alicyclic ring is cyclopentyl or cyclohexyl.

The heterocyclic rings as used singularly or in combination with other groups include cyclic rings which may be saturated, partly unsaturated or heteroaryl, and contain one or two hetero ring atoms. The heterocyclic rings include the benzo heterocyclics. The heterocyclic ring contains from 5–14 ring atoms. It is preferred that the heterocyclic group contains 1, 2 or 3 heteroatoms selected from N, S or and contains at least 2 carbon ring atoms and up to a total of 13 ring carbon atoms and up to a total of 18 carbon atoms. It is preferred that the heterocyclic ring is monocyclic and contains 5 or 6 ring atoms. Typical examples include thienyl, furyl, tetrahydrofuryl, oxazolyl, benzoxazolyl, pyrrolyl, pyridyl, imidazoyl, benzothienyl, pyranyl, pyrazolyl, pyrazinyl, indolyl, pyrimidinyl, isoquinolyl, quinolyl, piperidyl, pyridazinal, indolinyl, morpholinyl and the like. The preferred heteroatoms are N, O, or S. In a preferred form the heterocyclic ring is a nitrogen containing heterocyclic ring. The especially preferred heterocyclic ring is a nitrogen containing heteroaromatic ring, such as imidazolyl, pyridyl, pyrrolyl, pyrazolyl, pyrimidinyl, pyrazinyl, pyridazinyl and the like.

The alkanoyl groups as defined herein contain from two to seven carbon atoms, one being the carbonyl carbon and the remainder being the alkyl portion. In a preferred embodiment alkanoyl is acetyl or pivaloyl or butyryl.

The preferred aroyl is benzoyl.

In those situations wherein variables n or p is zero, as defined herein this defines a bond in the place of the respective group. On the other hand, when q is 0, this defines a hydrogen in the place of the respective group, $(CHR_9)$.

The preferred R substituents are H, OH, or O—$R_{10}$ wherein $R_{10}$ is a lower alkanoyl or benzoyl or lower alkyl The preferred lower alkyl can have from one to four carbon atoms and the preferred alkanoyl is acetyl, butyryl, or pivaloyl.

The preferred $R_6$ is hydrogen.

When Y is

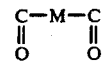

$R_2$ and X is $NR_6$, and $R_2$ is $OR_4$, $SR_4$, $NR_4R_5$, it is preferred that p is O.

It is preferred that R is OR$_4$, SR$_4$, or NR$_4$R$_5$ or NR$_4$R$_5$ or a covalent bond connected to X, thereby forming the cyclic structure shown herein. When R$_2$ is OR$_4$, SR$_4$ or NR$_4$R$_5$, it is preferred that R$_4$ is an alkyl group containing 2-4 carbon atoms and that R$_5$ is hydrogen or alkyl containing 2-4 carbon atoms.

It is preferred that R$_{15}$ is hydrogen, lower alkyl or a N-containing heterocyclic group. It is especially preferred that R$_{15}$ is hydrogen, alkyl containing 1-3 carbon atoms and a N-containing heteroaromatic group, as defined herein.

The preferred X groups are NR$_6$ or N. when R$_2$ represents a covalent bond connecting its adjacent carbonyl with X, the group

forms a heterocyclic ring having the formula:

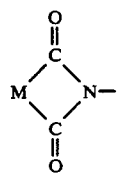

wherein M is as defined hereinabove. In this embodiment, ring A can be fused to the cyclic structure as follows:

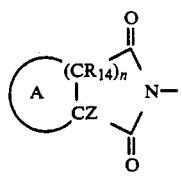

For example, ring A may can be an unsubstituted or substituted aromatic or nitrogen, oxygen, or sulfur containing heterocyclic ring system having from five to fourteen ring atoms in the ring(s) fused to M. Ring A may be monocyclic or bicyclic and may contain 1 or 2 heteroatoms. The preferred heteroatom is nitrogen. Ring A may be fused or spiro to the cyclic imide; when n=0, then ring A is spiro; when n=1, then ring A is fused. It is preferred that n=1 and Ring A is fused to the cyclic structure (See Formula IV hereinabove). In a preferred embodiment, R$_{14}$ and Z are hydrogen or both taken together form a covalent bond. The fused ring(s) can have 1 or more substituents and the substituents are lower alkyl, aryl, aryl lower alkyl, carboxyl, OR$_{10}$, SR$_4$, or NR$_4$R$_5$. In a preferred form the number of substituents is one or two.

A preferred embodiment thereof has the general formula:

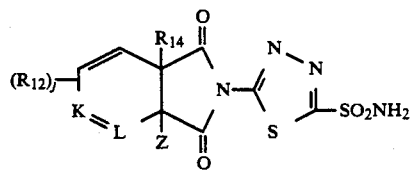

wherein K or L each independently is CH, N or S, j is one to four, and each R$_{12}$ is independently lower hydrogen alkyl, OH, SH or NH$_2$, and R$_{14}$ and Z are as defined hereinabove.

Similarly, when R$_{15}$ represents a covalent bond connecting its adjacent carbinol group with X, the group

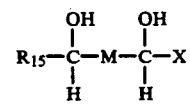

forms a heterocyclic ring having the formula:

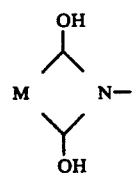

wherein M is as defined hereinabove. In this embodiment, ring A can be fused to the cyclic structure as follows:

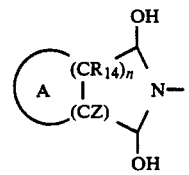

wherein n, Z and A are as defined hereinabove.

As before, in this diol formulation ring A may be unsubstituted or substituted aromatic or unsubstituted or substituted nitrogen, oxygen or sulfur containing heterocyclic ring system having from 5 to 14 ring atoms in the rings fused to M. Ring A may be monocyclic or bicyclic and may contain 1 or 2 heteroatoms. It is preferred that ring A is monocyclic and is pyridyl or imidazolyl. It is preferred that n is 1, i.e., ring A is fused to the ring.

DETAILED DESCRIPTION OF THE INVENTION

A preferred class of the invention are compounds having general formula II:

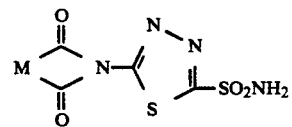

A preferred M is (CHR$_9$)$_p$ and each R$_9$ may be the same or different and may be H, OH or OR$_{10}$ wherein R$_{10}$ can be lower alkyl or lower alkanoyl, and the preferred p is two. The most preferred R$_9$ groups are H and OH.

When Y contains a carbonyl group, it is also preferred that M is HC=C(CHR$_9$)q CH=CR$_q$ and

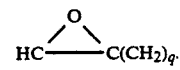

Especially preferred are compounds wherein q is zero.

Another preferred class are compounds having general formula III:

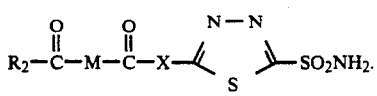

In this class, the preferred X is NR$_6$ and the preferred M is (CHR$_9$)$_p$.

In a more preferred form R$_9$ is H, and R$_2$ is OR$_4$.

In the most preferred embodiment of this species R$_4$ is H or ethyl, R$_6$ is H, and p is 0, 2, or 4.

The preferred compounds having general formula I are:

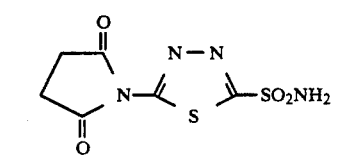 1

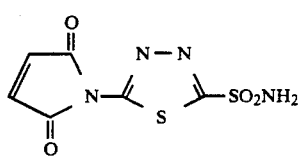 2

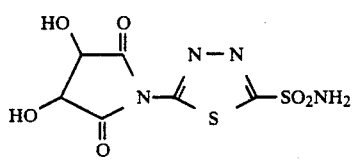 3

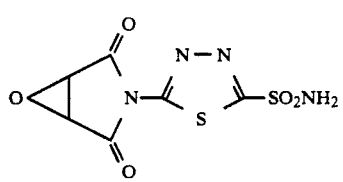 4

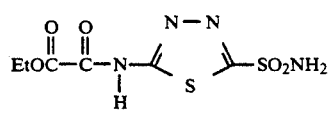 5

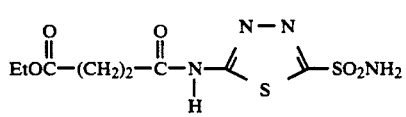 6

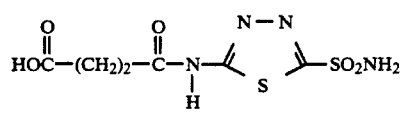 7

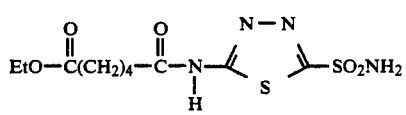 8

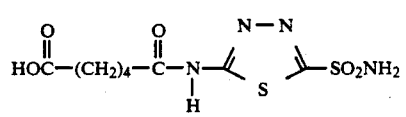 9

-continued

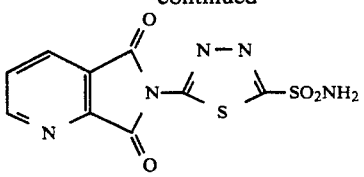 10

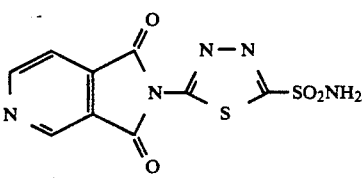 11

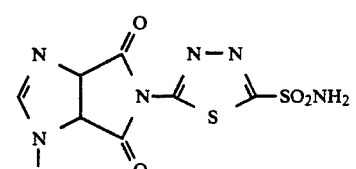 12

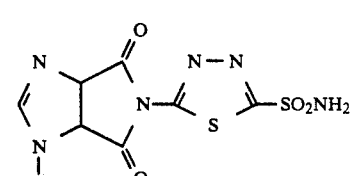 13

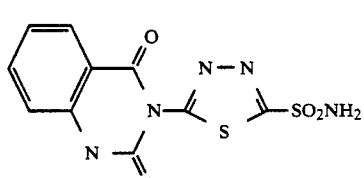 14

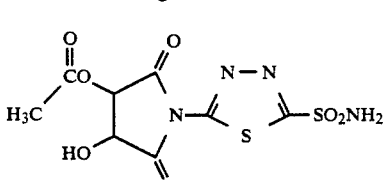 15

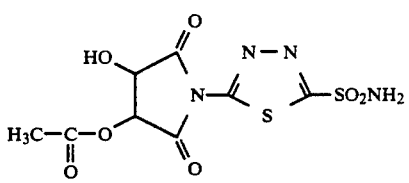 16

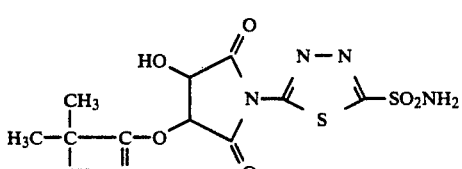 17

The compounds of the invention containing basic nitrogen form salts with acids, both organic and inorganic acids. Of particular value are salts with pharmaceutically-acceptable acids especially in dosage forms predicated on aqueous systems where the enhanced water solubility of the salts is most advantageous. Salts formed with pharmaceutically unacceptable acids are also useful in the isolation and purification of the basic nitrogen-containing new compounds. Salts include those formed with hydrochloric, sulfuric, nitric, perchloric, benzenesulfonic, toluenesulfonic, phosphoric, acetic, malic, malonic, tartaric and similar such acids.

The compounds of the invention also exist in stereoisomeric forms due to the presence of asymmetric centers in the molecule. This invention contemplates the stereoisomers individually or in mixtures or as the racemic mixture. The individual stereoisomers, can be obtained by standard resolution procedures known to those skilled in the art or by stereospecific synthesis.

The compounds or compositions of the present invention can be administered to the host in a variety of forms adapted to the chosen route of administration, i.e., orally, topically, intravenously, intramuscularly or subcutaneous routes. The preferred route of administration for ocular use is topical administration to the cornea.

In using the compounds or compositions of this invention for treatment of glaucoma topically, the compound may be carried in an inert, non-eye irritating, non-toxic eye drop diluent of conventional formulation. Such formulations are well known, and commonly referred to in, for example, the *Physician's Desk Reference for Ophthalmology* (1982 Edition, published by Medical Economics Company, Inc., Oridell, NJ), wherein numerous sterile ophthalmologic ocular solutions are reported, e.g., see pp. 112-114, which are incorporated herein by reference. For example, the drugs may be dissolved or suspended in a buffer containing a preservative (discussed infra.) and a viscosity agent, e.g., hydroxyalkylcellulose, such as hydroxyethylcellulose and hydroxypropylmethylcellulose.

Preferably the amount of the carbonic anhydrase inhibitors present in the eye drop treatment composition is a concentration of from about 0.25% to about 5% by weight of the eye drop treating composition. Most preferably, the amount is from about 0.5% to about 2.0% by weight of the eye drop treating composition, and in tests conducted to date, highly effective compositions have used the compounds at the 1% by weight suspension or solution level.

As heretofore mentioned, it is preferred that the diluent be an isotonic eye treatment carrier, buffered to a pH within the range of from about 4.0 to about 8.0 and containing a small but effective amount of a wetting agent and an anti-bacterial agent. The preferred pH range is from about 5.0 to about 7.8.

Commonly used wetting agents are well known, and again are mentioned in the previously referred to pages of the *Physician's Desk Reference for Ophthalmology*. One suitable one is Tween, and in particular, Tween 80. Likewise, anti-bacterials are known and commonly employed in such compositions. Suitable anti-bacterials include the most preferred benzalkonium chloride and others as well such as, for example, chlorobutanol. The amount of wetting agent can range from 0.01% to 0.10% by weight. The amount of anti-bacterial can range from about 0.004% to about 0.02% by weight of the eye drop treating composition.

The compounds of the invention may also be delivered by more sustained delivery devices including shields, wafers, inserts or other devices implanted or apposed directly to the cornea. The active compound may be associated with a shield, wafer or insert. By "association with", it is meant that the compound may be chemically bonded or physically incorporated with the shield, wafer or insert.

The compounds of this invention, are not only water soluble, but they also have a lipid solubility factor to allow transfer across the eye, and they have suitable structure to allow them to effectively function in the eye as carbonic anhydrase inhibitors per se, or following metabolic activation. Their water solubility means ease of preparation for topical application, their lipid solubility characteristics mean effectiveness in transfer across the cornea and into the target site (ciliary body).

With respect to the treatment of and prophylaxis of the other pathological diseases discussed hereinabove, such as osteoporosis as well as the prophylaxis and treatment of glaucoma, the active compound may also be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently contain an amount of active compound in such therapeutically useful compositions is such that a suitable dosage will be obtained. Preferred compositions or preparations according to the present invention are prepared so that an oral dosage unit form contains between about 50 and 500 mg of active compound. In a more preferred form, an oral dosage unit will contain from about 50 mg to about 100 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl propylparabens as preservatives, a dye and flavoring such as cherry or orange flavor. Of course, any material used preparing any dosage unit form should be pharmaceutically pure and substantially non-toxic in the amounts employed. In addition, the active compound may be incorporated sustained-release preparations and formulations.

The active compound may also be administered parenterally. Solutions of the active compound or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solution, the preferred methods of preparation are vacuum drying and the freeze-drying technique which yield a powder of the active ingredient plus any additional desired ingredient from previously sterile-filtered solution thereof The thiadiazole compounds outlined hereinabove can be made by techniques known to one skilled in the art. Exemplary procedures are outlined hereinbelow.

The compounds of the present invention can be prepared by art recognized techniques.

The compounds of the present invention having the formula (II):

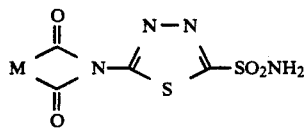

can be prepared from the reaction of 2-amino-1,3,4,thiadiazole-5-sulfonamide of the formula

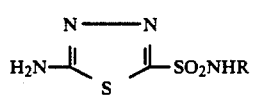

with the corresponding (a) dibasic acid, (b) anhydride, or (c) diacyl halide having the general formula:

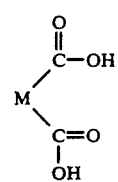

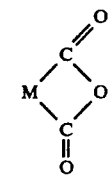

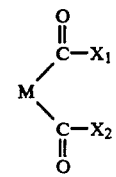

under suitable imide forming conditions thereby furnishing the compounds of formula II. In these definitions, R and M are as defined hereinabove and $X_1$ and $X_2$ are halides which can be the same or different. The halides (X) which can function in this reaction are well known to one skilled in the art. The preferred $X_1$ and $X_2$ are chlorine.

Compounds of Formula II can further be prepared using additional steps. For example, the initial bicyclic compound (2) is produced by a reaction of maleic acid, such as maleic acid, maleic anhydride or the diacid halide of maleic anhydride wherein the halide is F, Br or preferably Cl is reacted with 2-amino-1,3,4,-thiadiazole-5-sulfonamide as described above, under imide forming conditions to yield:

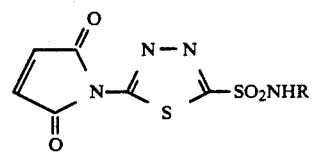

Further reaction of Compound 2 with oxidizing agents such as osmium tetraoxide and an alkylperoxide yields Compound 3,

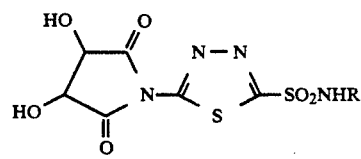

which is active per se. Under esterification procedures known to one skilled in the art, Compound 3 may be reacted with an acyl derivative of $R_{15}C$—OH such as an acid halide or anhydride wherein $R_{15}$ is H or lower alkyl. Under these conditions, Compound 3 may form a compound of the formula:

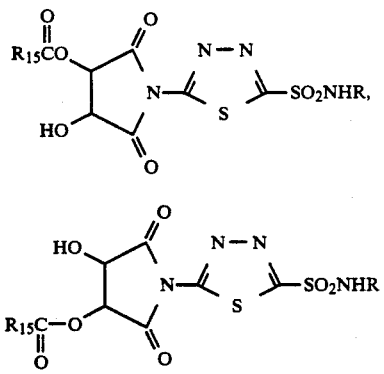

If compound of Formula 3 is reacted with an acylating derivative of

then a compound of the formula:

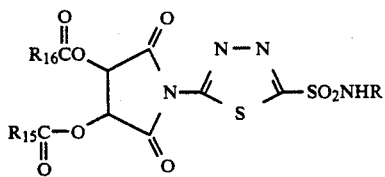   3 wherein $R_{15}$ and $R_{16}$ are independently, lower alkyl or H.

The compound of the present invention having the general formula III:

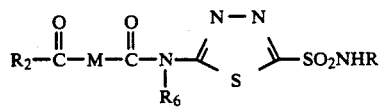   III can be prepared by reaction of 2-amino-1,3,4,thiadiazole-5-sulfonamide, described hereinabove, with the corresponding diacid derivative of the formula

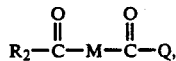

where Q is a halide or $OR_{12}$, OH, wherein M, $R_2$ and R are as defined hereinabove and $R_{12}$ is lower alkyl under amide forming conditions thereby furnishing the compounds of formula III.

In all of the reactions described hereinabove, the reaction is normally effected at or near room temperature or with slight heating, although temperature from 0° C. up to the reflux temperature of the reaction medium can be employed. The reaction is carried out in an inert solvent, such as methylene chloride, diethylether, dioxane, tetrahydrofuran and the like.

The reduced derivatives of the biscarbonyl compounds are formed from the corresponding dicarbonyl compounds of the formulae:

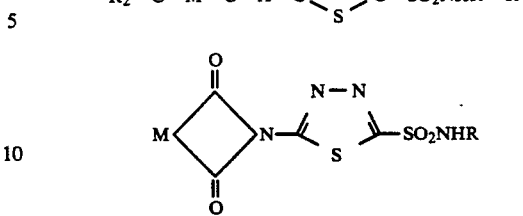

wherein X, M and R are as defined hereinabove and $R_2$ is $R_{15}$ by art recognized techniques known to one skilled in the art. More specifically, reducing agents, such as $LiAlH_4$, and the like can be used to effect the reduction of the two carbonyl groups and form the corresponding diol, respectively

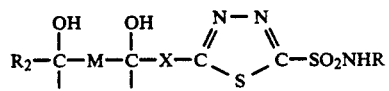   IV or

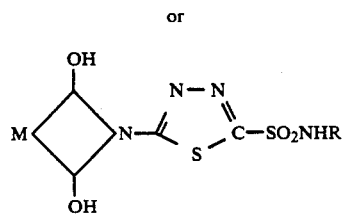   V

EXAMPLES

The invention will now be illustrated by examples. The examples are not intended to be limiting of the scope of the present invention. In conjunction with the general and detailed description above, the examples provide further understanding of the present invention and outlines a synthesis of a preferred embodiment of the invention.

The following examples represent preferred embodiments of the compositions of the invention and protocols for testing of (a) physiochemical properties;

(b) pharmacological evaluation of compounds as ocular hypotensive agents; and (c) evaluation of compounds for effect on cornea thickness.

The starting materials for the examples whose method of preparation are not indicated, are commercially available compounds which would be available from chemical supply houses well-known in the art such as Aldrich Chemical Co.

A. Synthetic Strategies and Physiochemical Properties

One reactant for compounds of classes II and III is 2-amino-1,3,4-thiadiazole-5-sulfonamide. This is prepared by hydrolysis of the acetamide 2-acetylamino-1,3,4-thiadiazole-5-sulfonamide (acetazolamide). A slurry of 0.2 mol of acetazolamide in 600 mL of methanol is treated with 60 mL 12N HCl. This mixture is heated with stirring to reflux for 6 hours. Reaction progress is monitored using liquid chromatography. If reaction is not complete after 6 hours, another 30 mL of 12N HCl is added, and the mixture held at reflux for 2 hours. Methanol is then removed under reduced pressure. Product is recovered after raising the pH of the suspension to 7 by addition of NaOH at 0-4°, followed by filtration.

Compounds of general formula II are prepared by condensation of difunctional acids, acylhalides or anhydrides with 2-amino-1,3,4-thiaziazole-5-sulfonamide. One example of this group is the formation of the maleimide. To a suspension of 0.1 mol of 2-amino-1,3,4-thiadiazole-5-sulfonamide in 100 mL of dry tetrahydrofuran, 0.1 mol maleic anhydride is added. The mixture is heated to 50° for 20 hours. Solvent is then removed under reduced pressure, and product is recrytallized from water, buffered (phosphate) at pH=7. The resulting maleimide is useful for further production of, for example, the corresponding diol, epoxide or various esters using standard techniques.

An example of the preparation of a compound of general formula III is as follows. To prepare 2-ethyl-succinamido-1,3,4-thiadizole-5 sulfonamide, a slurry of 28 mmol 2-amino-1,3,4-thiadiazole-5-sulfonamide is prepared in 150 mL dry THF containing 2.5 mL pyridine and maintained with stirring at room temperature. To this slurry a 10% solution of ethylsuccinylchloride in diethylether is added dropwise over 30 minutes. The mixture is stirred for 12 hours. To stop the reaction, 10 mL of $H_2O$ is added, organic solvent is vacuum-stripped, and the product precipitates upon chilling the resultant mixture.

The following examples further illustrate the invention.

In these examples the general methodology for testing these compounds is as follows. Melting point (M.P.) is assessed using a standard Fisher-Johns apparatus. Quantitative analysis of drug concentrations is carried out using either an enzymatic assay or by high performance liquid chromatography (HPLC). The enzymatic assay is a modification of Maren's micromethod, J. Pharmacol. Exp. Ther., 130:26-29, 1960. Essentially, a reaction volume of 0.8 mL, containing a carbonate/bicarbonate buffer, phenol red, purified carbonic anhydrase, and inhibitor is maintained at 0° degrees and saturation with $CO_2$ by constant bubbling. The time required for acidification to a color change endpoint is monitored as the dependent variable. Carbonic anhydrase inhibitors increase reaction time in proportion to their concentrations over a useful range. The HPLC analysis is performed using reverse phase chromatography ($C_{18}$) and gradient elution. At a flow rate of 2mL/min, initial mobile phase composition is 95% A, 5% B, where A is 50 mM phosphate buffer, pH=2, and B is $CH_3OH$. This composition is altered in a linear fashion over 12 minutes to a final composition of 5:95, A:B, v:v. Capacity factor (k') is determined using the relationship $k'=(V_3-V_o)/V_o$ where $V_e$ is the elution volume of the analyte of interest and $V_o$ is the void volume of the column. HPLC analysis using photodiode array UV-visible detection (400-200 nm) is also used to assess purity and acquire spectral information.

Solubility is determined by preparing saturated solutions of test compounds in pH=7.4 phosphate buffer followed by analysis of the solution for compound concentration.

Partition coefficients (PC) are determined by dissolving test compound in pH=7.4 phosphate buffer (saturated with the appropriate organic solvent) or organic solvent (diethyl ether or chloroform) saturated with buffer. Equal volumes of organic and aqueous solutions are added to test tubes which are then capped and mixed by inversion until equilibrium is achieved. The ratio of drug concentration organic: aqueous is the partition coefficient.

Corneal permeability rate constants ($k_{in}$) are determined in an in vitro system. Freshly excised bovine corneas are placed on 8 mm tissue culture wells (epithelial surface down) filled with tissue culture medium containing test compound. The well formed by the curvature of the cornea is filled with drug-free medium. Samples of medium are taken from the endothelial side for determination of drug concentrations. The rate constant for drug appearance is $k_{in}$. Enzyme inhibition is assessed by determination of $K_I$ versus carbonic anhydrase II using the enzymatic method. Accession rate is the product of $k_{in}$ and maximum buffer solubility. This is a useful estimate of delivery rate of drug to the anterior chamber of the eye following topical administration.

EXAMPLE 1

2-amino-1,3,4-thiadiazole-5-sulfonamide

This is prepared by hydrolysis of the acetamide 2-acetylamino-1,3,4-thiadiazole-5-sulfonamide (acetazolamide). A slurry of 0.2 mol of acetazolamide in 600 mL of methanol is treated with 60 mL 12N HCl. This mixture is heated with stirring to reflux for 6 hours. Reaction progress is monitored using liquid chromatography. If reaction is not completed after 6 hours, another 30 mL of 12N HCl is added, and the mixture held at reflux for 2 hours. Methanol is then removed under reduced pressure. Product is recovered after raising the pH of the suspension to 7 by addition of NaOH at 0.4°, followed by filtration. Yield is between 85 and 98% of theoretical with 99% purity. $K_I=40$ nM.

EXAMPLE 2

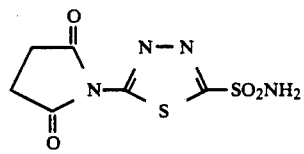

Succinylimidazolamide was prepared by adding a solution of 0.1 mol succinic anhydride, in 100 mL tetrahydrofuran (THF) to a suspension of 0.1 mol 2-amino-1,3,4 thiadiazole-5-sulfonamide. The slurry was stirred and heated to reflux for 48 hours. After addition of 10 mL volume water, THF was removed under reduced pressure. The above compound was obtained by filtration and 5 cycles of recrystallization from water in 22% yield. MW=264; k'=3.01; UV$\lambda_{max}$=254; solubility=10 mM; $k_{in}=2.1\times10^{-3}$/hr; accession rate=21 uM/hr.

EXAMPLE 3

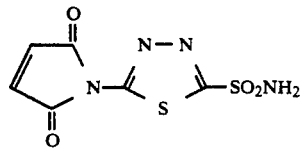

Maleimidiazolamide was prepared in the same manner as described in Example 3, by substituting maleic anhydride for succinic anhydride. Yield 12%; MW=262; $K_I=12$ nM; k'=3.06; UV $\lambda_{max}=254$; solubility=1 mM; $k_{in}=10.8\times10^{-3}$/hr; accession rate=10.8 uM/hr.

EXAMPLE 4

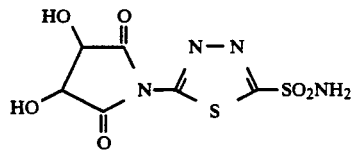

One mmol of the compound prepared in Example 3 was placed in a vial with 8 mmol t-butylhydroperoxide, 0.9 mL water, 0.1 mL tetraethylammonium hydroxide and 3 mg OsO₄. The tube was sealed for 24 hours at room temperature. The above-identified compound was recovered after washing the solution with hexane, followed by lyophilization. Recrystallization from water yielded a yellowish hygroscopic solid. $K_i=8$ nM; k'=0.71; UV$\lambda_{max}=260$; solubility>700 mM; $k_{in}=3\times10^{-5}$/hr; accession rate $\leq 21$ uM/hr.

EXAMPLE 5

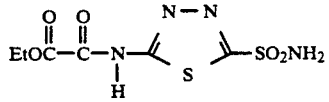

Ethyloxaloylazolamide (5) was produced as follows. 2-amino-1,3,4-thiadiazole-5-sulfonamide (0.09 mol) was added in 400 ml dry THF along with 0.11 mol pyridine. Ethyloxaloylchloride (0.09 mol in 100 mL diethyl ether) was then added slowly with stirring over about 30 minutes. After hours, 35 mL water was added, organic solvents were removed under reduced pressure. The resultant was chilled and filtered. Yield=69% of theoretical. $K_I=32$nM; k'=3.04; UV$\lambda_{max}=266$ nm; solubility=91 nm; $k_{in}=3.4\times10^{-3}$; M.P.=210° accession rate=309 uM/hr; PC (ether; water)=0.3; PC(CHCl₃: buffer)=0.23.

EXAMPLE 6

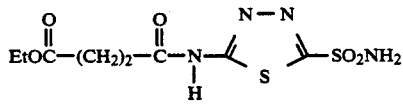

Ethylsuccinylazolamide (6) was synthesized as in Example 5, with substitution of ethylsuccinylchloride for ethyloxaloylchloride. Yield=45% of theoretical. $K_I=22$ nM; k'=3.65; M.P.=191°; UV $\lambda_{max}=266$ nm; solubility=5.8 mM; $k_{in}=15.5\times10^{-3}$/hr; accession rate=91 uM/hr; PC (ether: buffer)=0.35; PC (CHCl₃:buffer)=1.24.

EXAMPLE 7

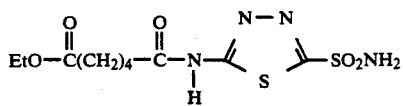

This was prepared from the compound formed in Example 9 by dissolving said compound in hot ethanol, then adding 0.1% BF₃ etherate. Solubility=0.2 mM; PC (CHC₃: buffer)=3.03; $k_{in}$in=$51.2\times10^{-3}$/hr; accession rate=26 uM/hr; $K_I=60$. Yield=80% after vacuum stripping then recrystallization from ethanol.

EXAMPLE 8

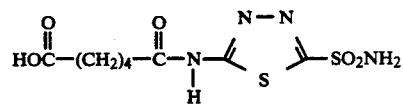

This is synthesized as follows. 67 mmol 2-amino-1,3,4-thiadizole-5-sulfonamide was added to 300 ml THF with stirring. 220 mmol adipic acid and 56 mmol dicyclohexylcarbodiimide was dissolved in THF. The second solution was added to the first ovet 10 minutes. Heat was applied and the reaction was held at reflux for 6 hours. The resultant was cooled to 4–10° and filtered, then solvent was removed under reduced pressure. The recovered solid is then recrystallized 3x from methanol. Solubility=0.5 mM, PC (ether) 3.56, $K_I=60$ nM.

similarly, using the procedures described hereinabove and the appropriate reagents, the following compounds can also be synthesized:

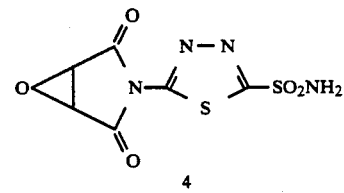

4

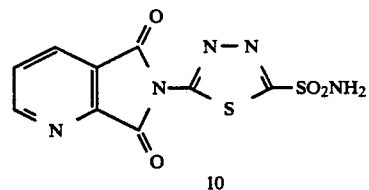

10

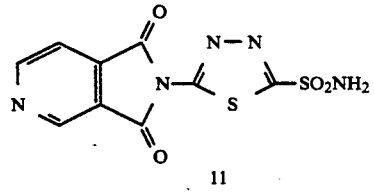

11

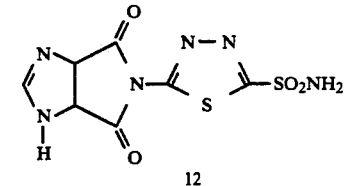

12

19
-continued

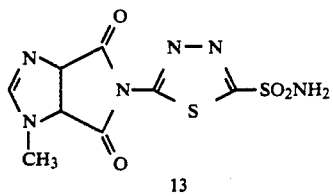
13

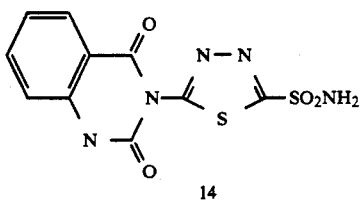
14

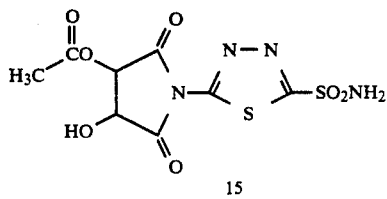
15

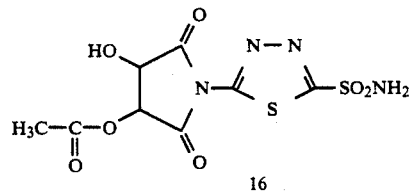
16

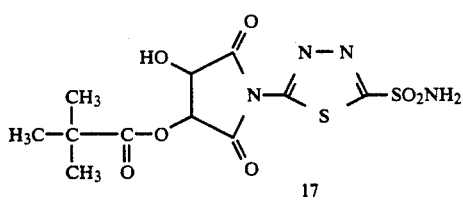
17

B. Protocol for Evaluation of Compounds as Ocular Hypotensive Agents

B.1 Ocular Hypotensive Effects Following systemic Administration

Compounds are dissolved in corn oil and injected subcutaneously into New Zealand albino rabbits. Corn animals receive an injection of corn oil alone, experimental animals receive a dose of 225 μmol in 1 mL. Injection time is defined as t=0. At t=20, 35, 60, 75, 90, 110, 150 and 180 minutes, intraocular pressure (IOP) is measured using application penutonometry. Results from representative experiments are shown in Table 1. Values shown are IOP in mm Hg represented as the mean (S.D.) of n replications. Data are analyzed using Student's t-test for unpaired data. For time points marked with asterisks, p<0.05, which is taken to indicate a difference from vehicle treated controls.

TABLE 1

| Time (min) | Compound | | | Corn Oil Vehicle |
|---|---|---|---|---|
| | 5 | 6 | 8 | |
| 0 | 18.4(1.9) | 18.3(1.0) | 18.3(1.9) | 18.1(1.6) |
| 20 | 17.5(2.1) | 17.5(2.0) | 17.0(2.6) | 18.4(2.3) |
| 45 | 15.0(2.6)* | 15.4(2.1)* | 12.9(3.6)* | 18.9(1.4) |
| 60 | 14.5(2.2)* | 13.7(1.6)* | 12.0(3.5)* | 19.3(1.4) |
| 75 | 14.6(5.1) | 12.4(1.9)* | — | 17.7(2.0) |

TABLE 1-continued

| Time (min) | Compound | | | Corn Oil Vehicle |
|---|---|---|---|---|
| | 5 | 6 | 8 | |
| 90 | 17.8(1.7) | 15.1(2.0)* | 13.1(2.6)* | 19.6(2.7) |
| 110 | 17.3(2.2) | 15.0(1.8)* | 14.6(2.1)* | 20.3(1.5) |
| 150 | 18.3(1.3) | 16.6(1.6) | 14.9(2.8)* | 18.6(1.6) |
| 180 | | | 15.6(2.2)* | 18.7(0.9) |
| | n = 10 | n = 9 | n = 8 | n = 8 |

B.2 Ocular Hypotensive Effects Following Topical Administration

New Zealand white rabbits were used to assess the ability of the compounds of this invention to lower IOP. IOP was determined using rabbits familiarized with the Alcon pneumotonometric measurement employed. Drugs were dissolved or suspended in 0.9% saline or a 1% hydroxypropylmethyl-cellulose gel and instilled into one eye. The contralateral eye received the vehicle only, thereby serving as a control. Initial screening was accomplished using measurements every 15-30 minutes for 5-6 hours. Statistical analysis wa then performed using Student's t-test for paired data (two-tailed).

The compounds of this invention have shown efficacy for the reduction of IOP as shown in Table 2.

TABLE 2

IOP LOWERING ACTIVITY OF VARIOUS HETEROCYCLIC SULFONAMIDES

| Compound | Maximum Topical Effect (mm Hg) | Time to Peak effect (min) | Duration (hr) |
|---|---|---|---|
| Succinyl-imidazolamide (1) | −2.3 ± 1.7 | 30 | 2 |
| Maleimid-azolamide (2) | −2.0 ± 0.5 | 60 | 3 |
| Dihydroxysuccin-imidazolamide (3) | −4.0 ± 0.7 | 60 | 6+ |
| ethyloxalazol-amide (5) | −3.0 ± 0.7 | 75 | 5+ |
| ethylsuccinylazol-amide (6) | −2.2 ± 0.8 | 30 | 2 |
| ethyladipoylazol-amide (8) | approx. −1.0 | 30 | 2 |

C. Assessment of Corneal Effects

The cornea is lined on its posterior aspect by an endothelial cell layer. This endothelium serves to maintain corneal clarity, in part due to the action of carbonic anhydrase. After (e.g., in conjunction with cataract surgery) it would be beneficial to have a functional test for corneal competence. These agents, when applied topically lead to a mild, transient swelling of the cornea which can readily be assessed by pachymetry. A competent cornea will return to normal thickness rapidly, while a compromised cornea (depressed endothelial function) will not recover as rapidly. This compromised patient is then a candidate for immediate corneal transplant, obviating the need for future inevitable surgery.

The above preferred embodiments and examples are given to illustrate the scope spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A method for treating glaucoma in mammals comprising administering to a mammal in need of such treatment an ocular hypotensive effective amount of a compound having the formula:

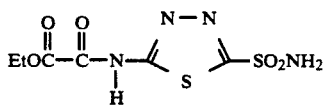

2. A method for treating glaucoma in mammals comprising administering to a mammal in need of such treatment an ocular hypotensive effective amount of a compound having the formula:

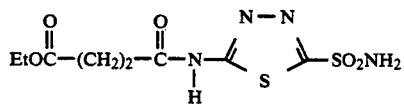

3. A method for treating glaucoma in mammals comprising administering to a mammal in need of such treatment an ocular hypotensive effective amount of a compound having the formula:

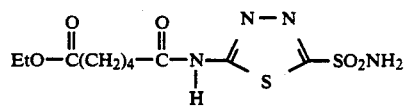

4. A method for treating glaucoma in mammals comprising administering to a mammal in need of such treatment an ocular hypotensive effective amount of a compound having the formula:

* * * * *

UNITED STATES PATENT AND TRADEMARK OFFICE
CERTIFICATE OF CORRECTION

PATENT NO. : 5,242,937
DATED : September 7, 1993
INVENTOR(S) : William M. Pierce, Jr.

It is certified that error appears in the above-indentified patent and that said Letters Patent is hereby corrected as shown below:

In the Abstract, line 4: "X-Y" should read --Y-X--

Column 1, lines 41-42: after "antagonists" insert --.--

Column 1, line 46: after "(CA)" insert --.--

Column 1, line 55: after "efficacy" insert --.--

Column 2, line 55: insert --Y is--

Column 3, line 11: "alkyny" should read --alkynyl--

Column 3, line 54: "n is or 1" should read --n is 0 or 1--

Column 4, line 29: after "or" insert --O--

Column 4, line 57: after "alkyl" insert --.--

Column 5, line 1: "R" should read --$R_2$--

Column 5, line 2: delete "NR4R5 or"

Column 11, line 6: after "exists" insert --.--

UNITED STATES PATENT AND TRADEMARK OFFICE
CERTIFICATE OF CORRECTION

PATENT NO. : 5,242,937           Page 2 of 3
DATED : September 7, 1993
INVENTOR(S) : William M. Pierce, Jr.

It is certified that error appears in the above-indentified patent and that said Letters Patent is hereby corrected as shown below:

Column 12, line 30: "(X " should read --($X_1$)--
Column 15, line 56: "$V_3$" should read --$V_e$--
Column 17, line 30: "$\geq$" to read --$>$--.
Column 17, line 44: before "hours" insert --18--

Column 18, line 12: "($CHC_3$" should read --($CHCl_3$--

Column 18, line 33: "similarly" should read --Similarly--

UNITED STATES PATENT AND TRADEMARK OFFICE
CERTIFICATE OF CORRECTION

PATENT NO. : 5,242,937
DATED : September 7, 1993
INVENTOR(S) : William M. Pierce, Jr.

It is certified that error appears in the above-indentified patent and that said Letters Patent is hereby corrected as shown below:

```
Column 19, line 52:  "35"  should read --45--
COlumn 20, line 17:  delete -- - --
Column 20, line 21:  "wa"  should read --was-
```

Signed and Sealed this

Eleventh Day of July, 1995

*Attest:*

BRUCE LEHMAN

*Attesting Officer*  *Commissioner of Patents and Trademarks*